United States Patent [19]

Furlow et al.

[11] 4,244,370
[45] Jan. 13, 1981

[54] TOOL FOR POSITIONING IMPLANTABLE MEDICAL PROSTHETIC DEVICE AND METHOD OF USING SAME

[75] Inventors: William L. Furlow, Rochester; Michael A. Mikulich, St. Paul, both of Minn.

[73] Assignee: American Medical Systems, Inc., Minneapolis, Minn.

[21] Appl. No.: 962,319

[22] Filed: Nov. 20, 1978

[51] Int. Cl.³ ............................ A61B 17/00; A61F 5/00; A61B 17/34
[52] U.S. Cl. ................................ 128/303 R; 128/79; 128/329 R; 128/DIG. 20; 128/334 R
[58] Field of Search ............... 128/334, 343, 217, 264, 128/79, 218 C, 330, 419, 642, 215, 303 R, 303 A, 303 B, 329 R, DIG. 20, 130, 303.19

[56] References Cited

U.S. PATENT DOCUMENTS

| Re. 27,645 | 5/1973 | Drummond et al. | 128/218 C |
|---|---|---|---|
| 2,704,541 | 3/1955 | Wyatt | 128/303R |
| 2,738,790 | 3/1956 | Todt, Sr. et al. | 128/334 R |
| 2,788,787 | 4/1957 | Trace | 128/303 R |
| 3,608,539 | 9/1971 | Miller | 128/329 |
| 3,998,230 | 12/1976 | Miller | 128/330 |
| 4,010,757 | 9/1977 | Jula et al. | 128/419 P |
| 4,050,459 | 9/1977 | Sanchez | 128/218 C |

FOREIGN PATENT DOCUMENTS 456976 of 1947 Canada ................................ 128/218 C Primary Examiner—Robert W. Michell
Assistant Examiner—C. W. Shedd
Attorney, Agent, or Firm—Williamson, Bains, Moore & Hansen

[57] ABSTRACT

The tool comprises a hollow barrel having an obturator slidably mounted therein and having a rounded forward end. A locating device is attached to the barrel to stabilize the obturator in the plurality of predetermined positions as it is moved along the bore of the barrel. A needle having suture material attached may be placed within the bore of the barrel. A slot is located along the length of the barrel to allow the suture material to exit from the side of the barrel. In practice, the tool may be inserted into a bodily structure such as one of the corpora cavernosa of a penis. The outer surface of the barrel is equipped with a plurality of markings that allow the user to gauge the depth that the barrel has been inserted into a bodily structure. After the tool is inserted, the obturator is slid along the barrel bore to force the needle out of the rounded forward end of the barrel. The needle is manually pulled out of the bodily structure. After the tool is withdrawn, suture material remains threaded through the bodily structure.

5 Claims, 6 Drawing Figures

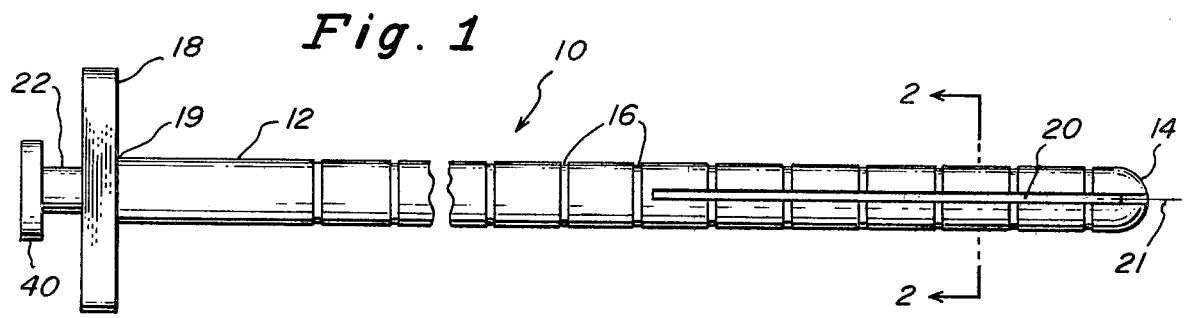
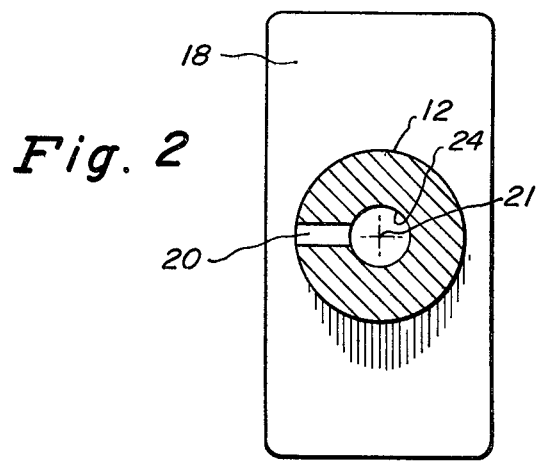
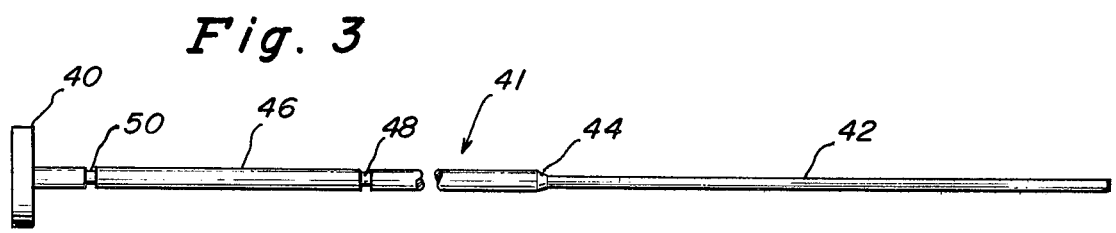
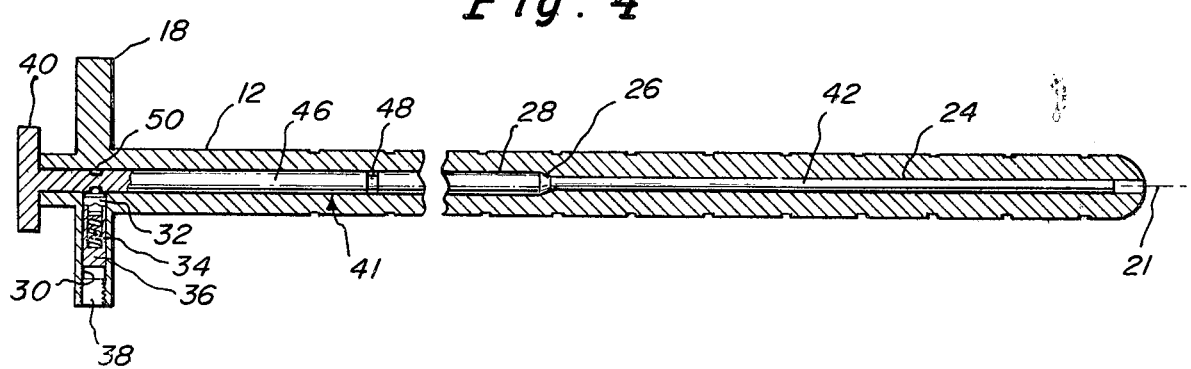

TOOL FOR POSITIONING IMPLANTABLE MEDICAL PROSTHETIC DEVICE AND METHOD OF USING SAME

BACKGROUND OF THE INVENTION

1. Field of the Invention

This invention relates generally to medical systems, and pertains more particularly to a tool and method of using a tool for the implantation of urological prosthetic devices.

2. Description of the Prior Art

Various techniques have been developed for the implantation of urological prosthetic devices using tools such as forceps or dilators. One type of prosthetic device which may be implanted using this tool is described by Robert Buuck in U.S. Pat. No. 3,954,102 which discloses a penile erection system. Column 6, lines 28 through 34 of that patent, describe the use of a rigid metal rod to dilate the corpora cavernosa regions of the penis to allow insertion of inflatable prosthetic cylinders.

One known method for inserting inflatable prosthetic devices involves the use of long silicone shod vascular forceps. The forceps is used to grasp the tip of an inflatable cylinder. The forceps is then forced into the corpus cavernosum, thereby also pulling the inflatable cylinder into the corpus cavernosum. Once the inflatable cylinder is in position, the grip of the forceps is released and it is withdrawn from the corpus cavernosum. One disadvantage noticed with this procedure is that considerable skill is required to ensure that the inflatable cylinder remains in place as the forceps is withdrawn.

Another technique previously used for the insertion of inflatable cylinders into the corpora cavernosa includes the steps of freezing a liquid within the cylinders, forcing the now rigid cylinders into the corpora cavernosa, and subsequently thawing the cylinders. This technique is undesirable in that the inflatable cylinder may be damaged by the freezing temperatures and the steps necessary consume unreasonable amounts of time and are unreasonably expensive.

A third known method for inserting inflatable cylinders into the corpora cavernosa includes the use of a tool preferably in the form of a rod. This rod is capable of being releasably attached at one end to the tip of the inflatable cylinder. In practice, the rod is pushed into the corpus cavernosum thus pulling the inflatable cylinder along. Attachment between the rod and the inflatable cylinder is preferably a length of suture tied in a snare such that pulling on a free end of the suture outside the corpus cavernosum will release the rod from the inflatable cylinder. After the rod has been inserted, the snare is released and the rod is withdrawn from the corpus cavernosum, leaving the inflatable cylinder inside the corpus cavernosum. This method is undesirable since tearing of the septum may result when the rod and snare are pushed inside the corpus cavernosum. Another disadvantage of this technique is that the inflatable cylinder is exposed to abrasive contact when the rod is withdrawn past the cylinder. A further disadvantage is that the presence of the rod and the inflatable cylinder in the corpus cavernosum simultaneously may overdilate the tunica albuginea and may cause a ballooning effect.

The basic drawback to the three methods described above is the large amount of manual effort required to maintain the inflatable cylinder in the desired position inside the corpus cavernosum during the time that the distal end of the cylinder is being inserted into the penile crus. It is generally desirable to maintain the tip of the inflatable cylinder within the glans penis. In order to do this, it is necessary to grasp the tip of the cylinder and trap it with the fingers through the tissues of the penis. Generally, this manual trapping of the tip of the cylinder has been difficult to accomplish.

SUMMARY OF THE INVENTION

Accordingly, an object of the present invention is to provide a tool and a method of using the tool for implanting medical prosthetic devices and for other medical procedures.

Another object is to reliably position prosthetic implants at stable locations inside the body. One example of the use of this technique is to maintain the tip of an inflatable cylinder in place within one of the corpora cavernosa. Another example is the use of this technique to reliably locate a hydraulic pump within the dependent portion of the scrotum. One further example of the use of this technique is to place a prosthetic testicle in a desired location.

A further object of the invention is to provide a tool for simultaneous dilation of a corpus cavernosum, measurement of corpus cavernosum length, and threading of suture material through the glans penis.

Another object of the invention is to minimize tearing of the septum when an inflatable cylinder is inserted inside a corpus cavernosum.

A further object of the invention is to provide a method for inserting an inflatable cylinder inside the corpus cavernosum which prevents the tunica albuginea from being overdilated and thus avoids the ballooning effect.

Another object is to provide a tool for use in inserting both the distal end of an inflatable cylinder into the glans penis and the proximal end into the crus.

A further object of the invention is to minimize abrasion to the suture materials used, thus preventing suture failure.

Another object is to avoid damaging the medical prosthetic devices by minimizing abrasive contact between the devices and other objects. Even small amounts of abrasive contact may cause some devices to eventually fail in use.

Still further, an object of the invention is to simplify the operating procedure for implanting medical prosthetic devices and reduce the time and expense required.

Briefly, the invention involves the implanation of medical prosthetic devices and the performance of other surgical procedures within living bodies. A tool for use in implantation procedures allows material to be threaded through a body structure. The tool includes a hollow barrel capable of receiving a needle within its bore. The barrel is equipped with surface markings allowing the determination of the depth to which the tool has been inserted inside the body structure. An obturator is provided which slidably mounts inside the barrel of the tool. As the obturator is slid into the handle end of the barrel, the needle is forced out of the rounded forward end of the barrel. In use, the rounded forward end of the barrel is inserted into a bodily structure and the depth of insertion is measured. Subsequently, the barrel is positioned so as to allow the needle to project through the outer covering of the bodily structure when the obturator is slid into the barrel bore. Then the needle is grasped from outside the bodily structure and pulled free thereby pulling suture material outside the bodily structure. When the barrel is withdrawn from the bodily structure, a length of suture material is left threaded through the bodily structure from the point of insertion of the barrel to the point of exit of the needle. An implantable medical device may be attached to the suture material and drawn into the bodily structure at the point where the barrel was previously inserted. Positioning of the prosthetic device within the bodily structure is accomplished by pulling on the free end or ends of the suture material previously attached to the needle. The medical prosthetic device may be maintained in place by applying appropriate forces to the free end or ends of the suture material.

DESCRIPTION OF THE DRAWINGS

FIG. 1 is a side elevation view of the tool for implanting medical prosthetic devices;

FIG. 2 is a cross sectional view taken in direction of line 2—2 of FIG. 1 for the purpose of illustrating structure of the barrel portion of the tool;

FIG. 3 is a side elevation view of the obturator portion of the tool;

FIG. 4 is a side sectional view of the tool of FIG. 1;

DESCRIPTION OF THE PREFERRED EMBODIMENT

Figure 5:
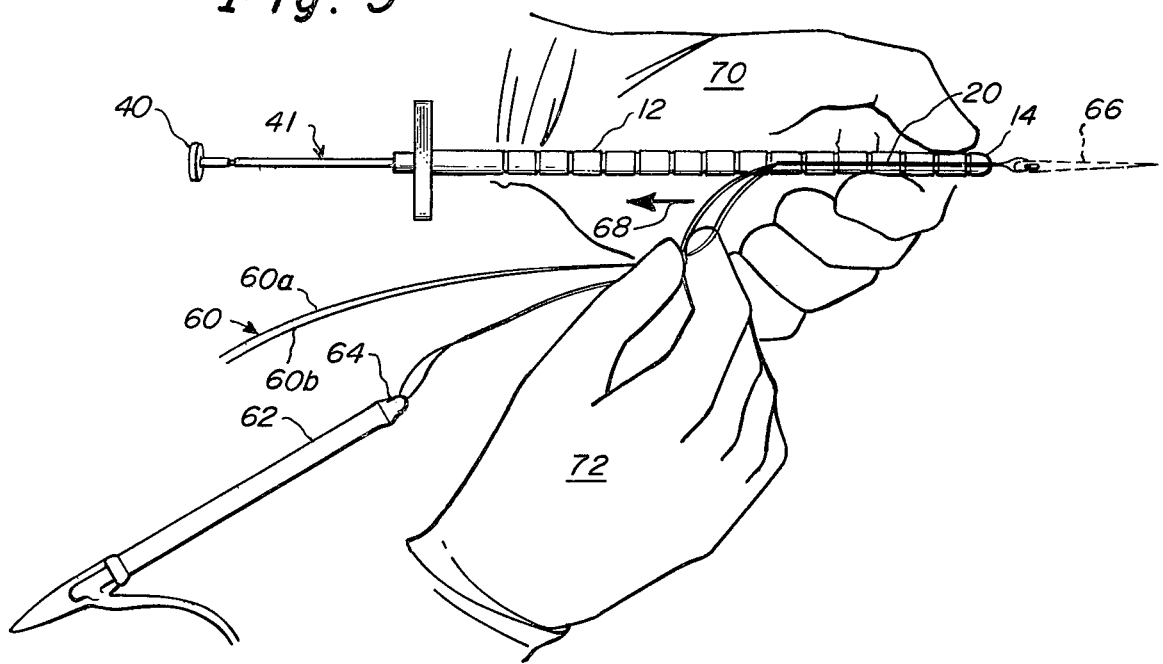
FIG. 5 illustrates a suture strand looped through an implantable medical device and shows the tool in use prior to the time when the barrel is inserted into the corpus cavernosum.

Referring first to FIG. 1, the tool for inserting medical prosthetic devices has been denoted generally by the reference numeral 10. The barrel 12 of the tool 10 has a rounded forward end 14 which allows insertion into a bodily cavity. Markings 16 are applied to the outer surface of barrel 12 to allow the user to determine the depth that barrel 12 has been inserted into a bodily davity. Markings 16 are preferably made by cutting circumferential grooves in the barrel 12. Barrel handle 18 is attached to the handle end 19 of the barrel 12. A barrel slot 20 is cut parallel to the axis 21 of barrel 12. Support 22 is attached to barrel handle 18 and abuts against obturator handle 40.

Referring now to FIG. 2, forward bore 24 is shown centered on the axis 21 of barrel 12. As shown, slot 20 communicates with forward bore 24.

Referring next to FIG. 3, an obturator is referred to generally by the reference numeral 41. Obturator handle 40 is attached to rearward shaft 46 which has a retraction groove 48 and an extension groove 50. Rearward shaft 46 is attached to a tapered section 44 which is attached to a forward shaft 42.

As shown in FIG. 4 of the drawings, the obturator 41 fits within the barrel 12 and is capable of sliding along the barrel axis 21. When the obturator 41 is removed from the barrel 12, empty space within the barrel 12 is defined by forward bore 24, tapered bore 26, and rearward bore 28. Obturator 41 is slidably pulled out of barrel 12 by grasping and manually pulling obturator handle 40 away from barrel handle 18. A plurality of stable, predetermined positions of obturator 41 with respect to barrel 12 are defined by a plurality of spaced apart grooves on rearward shaft 46 of obturator 41. shown in the drawing as retraction groove 48 and extension groove 50. Plunger 32 mounts inside plunger housing 36 and is forced towards rearward shaft 46 by the resilient member 34. Resilient member 34 is preferably a helical coil spring mounted inside plunger housing 36. Plunger housing 36 is preferably threadably mounted in transverse bore 30 of barrel handle 18. Plug 38 is inserted in transverse bore 30 to prevent contaminants from entering and interfering with the movement of plunger 32. In use, plunger 32 moves in and out of grooves 48 and 50 on rearward shaft segment 46 as obturator 41 is slid inside the barrel 12. Cooperation between plunger 32 and retraction groove 48 or extension groove 50 provides stable positions as obturator 41 is slid inside the barrel 12. When plunger 32 contacts retraction groove 48, the obturator 41 is said to be restrained in a "retracted" position, and a needle may be placed inside forward bore 24, as described further hereinafter. When plunger 32 contacts extension groove 50, the obturator 41 is said to be restrained in an "extended" position, and the needle previously placed inside forward bore 24 is forced out by contact with forward shaft 42, as described further hereinafter. For smooth mechanical operation, it is desirable that forward shaft segment 42 fit closely within forward bore 24 and that forward bore 24 be slightly larger in diameter than the maximum outer dimensions of the needles used. It is desirable that rearward shaft segment 46 be larger in diameter than forward shaft segment 42 so that rearward shaft segment 46 remains strong and rigid when grooves 48 and 50 are cut. For smooth mechanical operation, it is desirable that rearward shaft segment 46 fit closely within rearward bore 28. Tapered section 44 is used to smoothly connect rearward shaft segment 46 to forward shaft segment 42 and prevent stress risers. Similarly, tapered bore 26 smoothly connects rearward bore 28 to forward bore 24.

Referring now to FIG. 5, the method of inserting a needle 66 in the barrel 12 is illustrated. A strand of suture material 60 is looped through the point of attachment 64 of the implant 62, here shown as an inflatable penile prosthesis as described by Robert Buuck in U.S. Pat. No. 3,954,102. Both free ends of the strand of suture material 60 are then passed through needle 66, here shown in phantom 66. Suture material 60 is then placed inside barrel slot 20 of barrel 12 in the manner shown in FIG. 5. Barrel 12 may be held by the left hand 70 and the suture material may be pulled by the right hand 72 in the direction of the arrow 68. If the obturator 41 has been "retracted" by pulling on obturator handle 40, the needle 66 will be forced into the barrel 12. When needle 66 is inside barrel 12, suture 60 exits from barrel 12 through the barrel slot 20 and the barrel is ready for insertion into a bodily cavity, the corpus cavernosum in this case.

After the needle 66 has been inserted in the barrel 12, the barrel 12 is ready for insertion in a bodily cavity. A specific use for this tool contemplated by the inventor is the implantation of inflatable prostheses into the corpora cavernosa of a penis. When used for such a purpose, the barrel 12 is first used to dilate and measure the depth of the distal portion of one of the corpora cavernosa. All surfaces of barrel 12 are smooth to avoid abrasive contact with internal penile structures. The barrel 12 is then used to dilate and measure the length of the proximal portion of one of the corpora cavernosa. The measurements of length of the proximal and distal portions of the corpus cavernosum are added together to determine the length of the inflatable penile prosthesis that is appropriate. This procedure of dilation and measurement is repeated for the second of the two corpora cavernosa. The needle 66 is then inserted in the barrel 12 as described above. The barrel 12 is then inserted into the distal portion of one of the corpora cavernosa thus leaving the implant 62 and the free ends 60a and 60b of the strand of suture material 60 outside the corpus cavernosum. The barrel 12 is advanced until the rounded forward end 14 of the barrel 12 is beneath the glans. The obturator handle 40 is then advanced until the obturator 41 reaches its "extended" position, thus forcing needle 66 out of the barrel 14 and through the glans. The needle 66 is then grasped from outside the body and pulled from the penis, thus leaving suture material 60 threaded through one of the corpora cavernosa. Needle 66 is pulled far enough from the penis to cause the free ends 60a and 60b of the strand of suture material 60 to exit from the penis. The barrel 12 is then withdrawn from the corpus cavernosum. The implant 62 is then drawn into the distal end of the corpus cavernosum by pulling on the two ends 60a and 60b of the strand of suture material 60. If the implant 62 is not in a satisfactory position, the implant 62 may be withdrawn from the corpus cavernosum and the barrel 12 may be reinserted to further dilate the distal portion of the corpus cavernosum. Once the implant 62 is in place beneath the glans, the two free ends 60a and 60b of the strand of suture material 60 are pulled to insure that implant 62 remains in place beneath the glans and to stretch the penis sufficiently to allow a portion of the implant 62 to be inserted into the distal portion of the corpus cavernosum.

Figure 6:
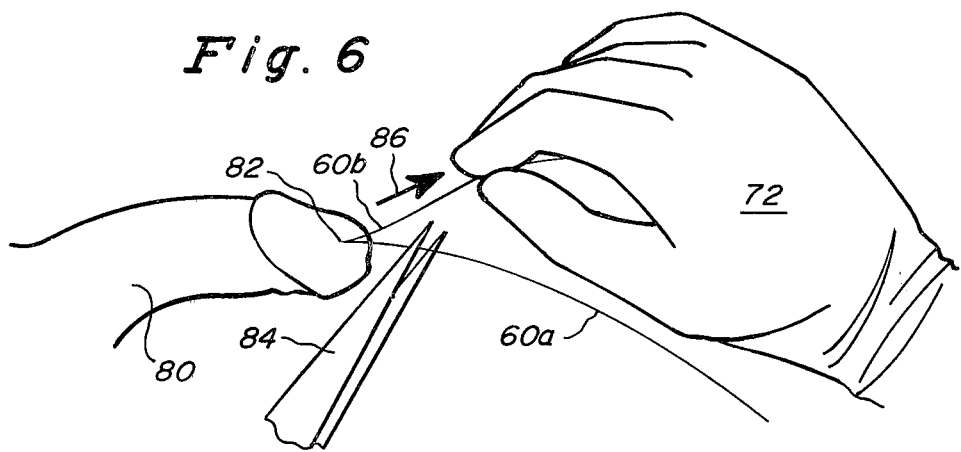
FIG. 6 illustrates the surgical procedure subsequent to the time when the barrel is removed from the corpus cavernosum.

Referring now to FIG. 6, the point of exit 82 of the suture material 60 from the glans is shown when the implant is positioned within a corpus cavernosum 80. To complete the implantation, one free end labeled 60a of the strand of suture material is cut with a scissors 84 and the other free end labeled 60b is pulled from the glans in the direction 86 by hand 72. The above described procedure is then repeated to insert another implant in the second of the two corpora cavernosa.

Applicant anticipates that the tool and method described herein may be used for such other medical purposes as surgically relocating body organs, particularly for the purpose of repositioning testicles. It is further anticipated that various changes may be made in the shape, construction, operation and method of use of the tool disclosed herein without departing from the spirit and scope of the invention as defined by the following claims.

What is claimed is:

1. A tool for the body implantation of medical prosthetic devices comprising:
   an elongated barrel capable of being inserted into an elongated bodily cavity and having a handle end and an opposite, forward end rounded for inserting into a bodily cavity;
   a central bore extending over the entire length of said barrel along the longitudinal axis thereof, said bore being of a diameter slightly greater than the maximum outer dimension of a suturing needle to be slidably inserted within said bore from said forward end of said barrel;
   an obturator slidably mounted inside of said bore in a close fit therewith for smooth back and forth sliding movement longitudinally of said bore between a retracted position wherein said obturator is moved towards said handle end of said barrel to permit a suturing needle to be inserted within said bore from said forward end of said barrel and an extended position wherein said obturator is moved towards said forward, rounded end of said barrel to project the needle with suture attached out of said bore from said forward end of said barrel; and
   an elongated slot extending along said barrel generally parallel to the longitudinal axis thereof from said forward end rearwardly towards said handle end, said slot further extending transversely through said barrel and communicating with said bore, whereby suture materials attached to a needle may be placed in said slot and passed into said bore and thence pulled towards said handle end of said barrel to draw the needle into said bore from said forward end of said barrel.

2. The tool of claim 1 including spaced apart markings along the length of said barrel permitting the user of said tool to gauge the depth to which said tool has been inserted in a bodily cavity.

3. The tool of claim 1 including means for restraining said obturator in said retracted and extended positions along the longitudinal axis of said barrel.

4. The tool of claim 3 wherein said obturator is in the form of an elongated shaft and said means for restraining said obturator along said barrel comprises:
   a pair of grooves at longitudinally spaced apart locations on the shaft of said obturator; and
   a plunger mounted on said barrel and resiliently urged towards said shaft for movement in and out of said grooves on the shaft of said obturator.

5. The tool of claim 4 wherein:
   a handle is mounted on said barrel at said handle end thereof and extends transversely to said barrel; and
   said plunger is positioned within said handle for transverse movement with respect to said barrel and said obturator shaft.

* * * * *